(12) United States Patent
Chiyonobu et al.

(10) Patent No.: US 7,759,122 B2
(45) Date of Patent: Jul. 20, 2010

(54) METHOD OF TESTING DENITRATION CATALYST

(75) Inventors: Tsuyoshi Chiyonobu, Hiroshima (JP);
Hatsumi Chiyonobu, legal representative, Shimonoseki (JP);
Hiroshi Shimada, Hiroshima (JP)

(73) Assignee: The Chugoku Electric Power Co., Inc., Hiroshima (JP)

( * ) Notice: Subject to any disclaimer, the term of this patent is extended or adjusted under 35 U.S.C. 154(b) by 874 days.

(21) Appl. No.: 11/630,796

(22) PCT Filed: Jun. 21, 2005

(86) PCT No.: PCT/JP2005/011381

§ 371 (c)(1),
(2), (4) Date: Dec. 27, 2006

(87) PCT Pub. No.: WO2006/001283

PCT Pub. Date: Jan. 5, 2006

(65) Prior Publication Data

US 2007/0243619 A1     Oct. 18, 2007

(30) Foreign Application Priority Data

Jun. 28, 2004     (JP) .............................. 2004-190106

(51) Int. Cl.
*G01N 31/10* (2006.01)
(52) U.S. Cl. ................. 436/37; 436/113; 436/116; 436/117; 436/118; 436/149; 436/151
(58) Field of Classification Search .............. 436/2, 436/37, 106, 113, 116–118, 149, 151, 181
See application file for complete search history.

(56) References Cited

U.S. PATENT DOCUMENTS 4,771,029 A * 9/1988 Pereira et al. ............... 502/355

(Continued)

FOREIGN PATENT DOCUMENTS

JP     4-338217     * 11/1992
JP     4-338217 A     11/1992

(Continued)

*Primary Examiner*—Arlen Soderquist
(74) *Attorney, Agent, or Firm*—Sughrue Mion, PLLC

(57) ABSTRACT

The present invention provides a method of testing an $NO_x$ removal catalyst, which method enables assessment of actual catalytic performance in consideration of gas flow condition in the gas conduits of the $NO_x$ removal catalyst. The method of testing a honeycomb-form $NO_x$ removal catalyst for use in a flue gas $NO_x$ removal apparatus, the catalyst having gas conduits for feeding a discharge gas from an inlet to an outlet of each conduit and performing $NO_x$ removal on the sidewalls of the conduit, wherein the method includes providing a first test piece, which is a portion of the catalyst having a length covering the entirety of a turbulent flow zone in which a gas to be treated that has been fed into the gas conduits through the inlet of the $NO_x$ removal catalyst forms a turbulent flow and further covering at least a portion of a laminar flow zone in which the turbulent flow is rectified to form a laminar flow; performing a first $NO_x$ removal test of the provided first test piece; subsequently, performing a second $NO_x$ removal test of a second test piece, which is obtained through cutting out a catalyst portion of a length covering the turbulent flow zone; and assessing, on the basis of the test results, catalytic performance of the turbulent flow zone and that of the laminar flow zone, whereby catalytic performance of the $NO_x$ removal catalyst is assessed.

7 Claims, 5 Drawing Sheets

U.S. PATENT DOCUMENTS

| | | | | |
|---|---|---|---|---|
| 5,546,004 A | * | 8/1996 | Schmelz | 324/446 |
| 5,693,295 A | * | 12/1997 | Foster | 422/180 |
| 5,972,254 A | * | 10/1999 | Sander | 264/39 |
| 6,145,302 A | * | 11/2000 | Zhang et al. | 60/274 |
| 6,195,986 B1 | * | 3/2001 | Davey et al. | 60/274 |
| 6,245,134 B1 | * | 6/2001 | Sandler | 96/417 |
| 6,803,236 B2 | * | 10/2004 | Bailey et al. | 436/37 |
| 6,833,272 B1 | * | 12/2004 | Binder et al. | 436/37 |
| 7,635,593 B2 | * | 12/2009 | Muzio et al. | 436/37 |
| 2006/0099110 A1 | * | 5/2006 | Shirakura | 422/62 |
| 2006/0154803 A1 | * | 7/2006 | Shirakura | 502/60 |
| 2007/0119053 A1 | * | 5/2007 | Shimada et al. | 29/890 |

FOREIGN PATENT DOCUMENTS

| | | | |
|---|---|---|---|
| JP | 5-123577 A | | 5/1993 |
| JP | 6-319951 A | | 11/1994 |
| JP | 2635664 B2 | | 4/1997 |
| JP | 2002-162393 | * | 6/2002 |
| JP | 2003-290630 | * | 10/2003 |
| JP | 2003-343814 A | | 12/2003 |
| JP | 2004-066228 A | | 3/2004 |
| JP | 2004-154622 A | | 6/2004 |
| WO | 0128665 A1 | | 4/2001 |
| WO | WO 2004/060561 A1 | | 7/2004 |

* cited by examiner

Relationship between percent NOx removal and catalyst site

Relationship between sustained turbulent flow distance and catalyst stain length

METHOD OF TESTING DENITRATION CATALYST

TECHNICAL FIELD

The present invention relates to a method of testing an $NO_x$ removal catalyst, which method is performed for the purpose of assessing performance of $NO_x$ removal catalysts employed in a flue gas $NO_x$ removal apparatus installed in a facility such as a thermal power station.

BACKGROUND ART

Conventionally, boilers provided in thermal power stations and a variety of large-scale boilers employing a fuel such as petroleum, coal, or fuel gas, waste incinerators, and similar apparatuses have been equipped with a flue gas $NO_x$ removal apparatus which contains a plurality of $NO_x$ removal catalyst layers.

The above employed $NO_x$ removal catalysts assume the form of honeycomb, plate, etc. During use, the catalytic performance of the catalysts is problematically deteriorated with elapse of time as a result of deposition, on the surface of the catalyst, of a substance which deteriorates the catalytic performance (hereinafter referred to as deteriorating substance) or through migration of the dissolved deteriorating substance into the catalyst.

Conventionally, the performance of the $NO_x$ removal catalysts has been managed by measuring $NO_x$ concentration and unreacted $NH_3$ concentration on the inlet and outlet sides of respective catalysts. When a drop in total performance of a catalyst system is confirmed, old catalysts are replaced with new catalysts or regenerated catalysts in order of use age, and such replacement is carried out periodically.

Generally, $NO_x$ removal catalysts are very expensive. Thus, there has been proposed one approach for prolonging the service life of the $NO_x$ removal catalysts to as long a duration as possible by assessing the performance of each unit catalyst (see, for example, Patent Document 1).

In the aforementioned case, when the catalytic performance is evaluated by the percent contribution calculated on the basis of the $NO_x$ concentration, the catalyst(s) having actually deteriorated performance cannot be detected correctly. Thus, there has been proposed a performance assessment method which provides assessment results reflecting the actual state of the catalyst more accurately, the method including determining $NH_3$ concentrations on the inlet and outlet sides of respective catalysts and taking into account the inlet mole ratio (i.e., inlet $NH_3$/inlet $NO_x$) (see, for example, Patent Document 2).

In an alternative performance evaluation method, instead of evaluating performance in an actual $NO_x$ removal apparatus, test pieces are cut out from an $NO_x$ removal catalyst, and the pieces are tested in a testing machine. For example, SV values based on catalyst amount and reacted gas amount, AV values based on catalyst surface area and amount of reacted gas, and other parameters may be obtained.

However, the aforementioned performance evaluation methods are developed without taking into account the flow of gas in the gas conduits, and overall catalytic performance of some $NO_x$ removal catalysts having a certain length cannot be fully evaluated.

Patent Document 1: Japanese Patent Publication (kokoku) No. 7-47108 (p. 2 to 3 and FIG. 1)

Patent Document 2: Japanese Patent Application Laid-Open (kokai) No. 2004-066228 (Claims and other sections)

DISCLOSURE OF THE INVENTION

Problems to be Solved by the Invention

Under such circumstances, an object of the present invention is to provide a method of testing an $NO_x$ removal catalyst, which method enables assessment of actual catalytic performance in consideration of gas flow conditions in the gas conduits of the $NO_x$ removal catalyst.

Means for Solving the Problems

Accordingly, a first mode of the present invention for attaining the aforementioned object provides a method of testing a honeycomb-form $NO_x$ removal catalyst for use in a flue gas $NO_x$ removal apparatus, the catalyst having gas conduits for feeding a discharge gas from an inlet to an outlet of each conduit and performing $NO_x$ removal on the sidewalls of the conduit, characterized in that the method comprises providing a first test piece, which is a portion of the catalyst having a length covering the entirety of a turbulent flow zone in which a gas to be treated that has been fed into the gas conduits through the inlet of the $NO_x$ removal catalyst forms a turbulent flow and further covering at least a portion of a laminar flow zone in which the turbulent flow is rectified to form a laminar flow;

performing a first $NO_x$ removal test of the provided first test piece;

subsequently, performing a second $NO_x$ removal test of a second test piece, which is obtained through cutting out a catalyst portion of a length covering the turbulent flow zone; and assessing, on the basis of the test results, catalytic performance of the turbulent flow zone and that of the laminar flow zone, whereby catalytic performance of the $NO_x$ removal catalyst is assessed.

According to the first mode, catalytic performance is evaluated in consideration of zone-dependent variation in gas flow condition in the gas conduits of the $NO_x$ removal catalyst, to thereby enable the user to recognize in an actual state of use more accurately.

A second mode of the present invention is drawn to a specific embodiment of the method of the first mode, wherein the turbulent flow zone has a length Lb (mm) represented by equation (A):

[F1]

$$Lb = a(Ly/Lys \cdot 22 e^{0.035(Ly \cdot Uin)}) \quad (A)$$

(wherein Uin (m/s) represents a gas inflow rate, Ly (mm) represents an aperture size, Lys is an aperture size of 6 mm (constant value), and "a" is a constant falling within a range of 3 to 6, when the aperture size (Ly) is 6 mm and the gas inflow rate is 6 m/s).

According to the second mode, the catalyst performance can be assessed more accurately by virtue of accurate determination of the length of the turbulent flow zone.

A third mode of the present invention is drawn to a specific embodiment of the method of the first or second mode, wherein the first or second $NO_x$ removal test is performed while a model gas having a composition simulating the gas treated in an actual $NO_x$ removal apparatus is fed at a gas inflow rate equivalent to that employed in an actual $NO_x$ removal apparatus, thereby determining catalyst performance.

According to the third mode, the catalyst performance can be assessed accurately by virtue of test conditions reflecting those employed in an actual $NO_x$ removal apparatus.

A fourth mode of the present invention is drawn to a specific embodiment of the method of the first or second mode, wherein the first or second $NO_x$ removal test is performed while a model gas having a composition simulating the gas treated in an actual $NO_x$ removal apparatus is fed at a flow rate differing from that employed in an actual $NO_x$ removal apparatus, thereby determining catalyst performance in consideration of the relationship between gas inflow rate and reacted $NO_x$.

According to the fourth mode, the relationship between gas inflow rate and reacted $NO_x$ is taken into account. Therefore, the catalyst performance can be assessed accurately, even though the model gas is fed at a flow rate differing from that employed in an actual $NO_x$ removal apparatus.

A fifth mode of the present invention is drawn to a specific embodiment of the method of any of the first to fourth modes, wherein the first or second $NO_x$ removal test comprises determining $NO_x$ concentrations on the inlet and outlet sides of respective test pieces; determining $NH_3$ concentrations on the inlet and outlet sides of respective test pieces; and determining percent $NO_x$ removal ($\eta$) on the basis of an inlet mole ratio (i.e., inlet $NH_3$/inlet $NO_x$).

According to the fifth mode, $NO_x$ concentrations and $NH_3$ concentrations are determined on the inlet and outlet sides of respective $NO_x$ removal catalysts, and the percent $NO_x$ removal ($\eta$) is determined on the basis of an inlet mole ratio. Therefore, the percent $NO_x$ removal, which is enhanced with increased mole ratio, can be evaluated accurately on an absolute basis.

A sixth mode of the present invention is drawn to a specific embodiment of the method of the fifth mode, wherein the percent $NO_x$ removal ($\eta$) is determined on the basis of $NH_3$ concentrations.

According to the sixth mode, the percent $NO_x$ removal ($\eta$) of respective $NO_x$ removal catalysts is determined on the basis of $NH_3$ concentrations rather than on the basis of $NO_x$ concentrations. Therefore, the catalytic performance can be more reliably assessed.

A seventh mode of the present invention is drawn to a specific embodiment of the method of the sixth mode, wherein the percent $NO_x$ removal ($\eta$) is determined on the basis of the following equation (1).

[F2]

$$\eta = \{(\text{inlet } NH_3 - \text{outlet } NH_3)/(\text{inlet } NH_3 - \text{outlet } NH_3 + \text{outlet } NO_x)\} \times 100 \times (\text{evaluation mole ratio/inlet mole ratio}) \quad (1)$$

According to the seventh mode, the percent $NO_x$ removal of each $NO_x$ removal catalyst can be accurately detected without variation.

EFFECTS OF THE INVENTION

According to the present invention, catalytic performance is evaluated in consideration of the turbulent flow zone on the inlet side of a $NO_x$ removal catalyst and the laminar flow zone on the downstream side. Thus, actual performance of the catalyst can be assessed accurately.

BEST MODES FOR CARRYING OUT THE INVENTION

Figure 1:
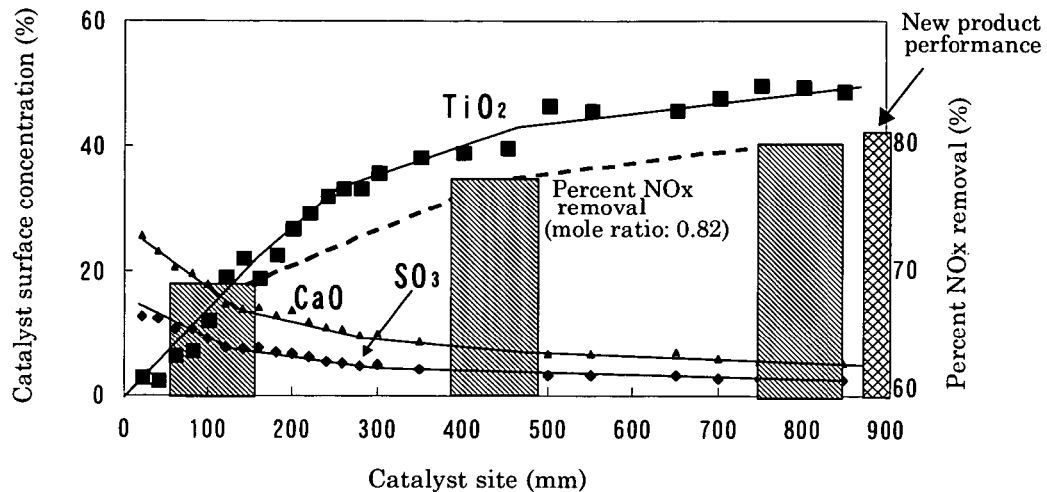
FIG. 1
A graph showing the results of Preliminary Test 1.

The present invention is applicable to any type of conventionally employed dust-through type $NO_x$ removal catalysts such as honeycomb catalysts. As used herein, the term "honeycomb catalyst" or "dust-through catalyst" refers to a catalyst unit including gas conduits having a cross-section of a polygon such as square, hexagon, or triangle, and performing catalytic reaction on the sidewalls of the gas conduits. No particular limitation is imposed on the form of the honeycomb catalyst, and typical forms include a cylinder containing gas conduits each having a hexagonal cross-section, and a rectangular prism containing gas conduits each having a square cross-section and arranged in a lattice-like form.

Conventionally, typical honeycomb $NO_x$ removal catalysts have a gas conduit pitch of 7 mm (aperture size: about 6 mm) and a length of about 700 mm to 1,000 mm. The present inventors have investigated the deterioration status of such catalysts after use along a longitudinal direction, and have found that the catalysts are more deteriorated on the inlet side than on the outlet side; the deterioration status is virtually unchanged in a portion ranging from the 300 mm site from the inlet to the outlet; and particularly, the catalysts are less involved in $NO_x$ removal reaction in a portion ranging from the outlet to the 300 mm site (from the outlet) than in a portion on the inlet side. The present invention has been accomplished on the basis of these findings. In other words, the present invention has been accomplished on the basis of the following finding by the inventors. Specifically, an exhaust gas is fed into an $NO_x$ removal catalyst through gas conduits as a turbulent flow, and $NO_x$ removal reaction is performed through contact of the gas with the sidewalls of the gas conduits. However, the flow of the thus-reacted exhaust gas is gradually straightened. Contact of the straightened gas flows (laminar flows) with the sidewalls of the conduits is minimized, thereby failing to attain effective $NO_x$ removal. Thus, catalytic performance cannot accurately assessed, if the reaction state in the turbulent flow zone and that of the laminar flow zone are not taken into account.

Furthermore, one conceivable mechanism that explains reduction in $NO_x$- or $NH_3$-removal efficiency is as follows. When an exhaust gas is fed from a wide space on the upstream side of the $NO_x$ removal catalyst to gas conduits of the catalyst, percent space of the gas is reduced from 1 to 0.6 to 0.7. The exhaust gas passes through the gas conduits while being in contact with the sidewalls of the conduits (catalyst surfaces) in a considerably turbulent state (in the turbulent flow zone). However, during the course of passage through the conduits, the gas flows are gradually regulated and straightened and mass transfer is controlled through diffusion only. After straightening, $NO_x$ molecules and $NH_3$ molecules which are to collide with the sidewalls decrease in number considerably. Thus, catalytic performance must be evaluated in consideration of sustained turbulent flow distance (i.e., index for the depth of a portion where the gas flow remains in a turbulent state) of the catalyst.

<Preliminary Test 1>

From a flue gas $NO_x$ removal catalyst which had been used for 50,000 hours in an actual flue gas $NO_x$ removal apparatus, catalyst portions (20 mm site to 850 mm site, from the inlet) were sampled in the longitudinal direction. $TiO_2$ concentration and concentrations of catalyst deterioration substances (CaO and $SO_3$) on the surface of each catalyst sample were determined.

Catalyst portions (50 mm×50 mm×100 mm in length) were cut from a catalyst included in each catalyst layer, and set in a performance testing machine. Portions at the 100 mm site, the 450 mm site, and the 800 mm site were tested. The test gas was fed at a mole ratio (inlet mole ratio=inlet $NH_3$/inlet $NO_x$) of 0.82 and an AV (amount of treatable gas per unit surface area of the catalyst) of 6.5, and percent $NO_x$ removal η was calculated on the basis of the aforementioned formula employing $NH_3$ concentration.

The results are shown in FIG. 1. As a reference product, a new (unused) catalyst was also measured in terms of percent $NO_x$ removal η.

The results indicate that the catalyst was severely deteriorated in a portion ranging from the inlet to the 300 mm site, and that a portion ranging from the 450 mm to the outlet exhibits percent $NO_x$ removal almost equal to that of a new catalyst product.

<Preliminary Test 2>

An $NO_x$ removal catalyst which had been used in an actual flue gas $NO_x$ removal apparatus was cut at the 600 mm site from the inlet (along the longitudinal direction), and the cut catalyst piece was set in a performance testing machine. Percent $NO_x$ removal η was determined at a plurality of sites at intervals of 100 mm under the following conditions: mole ratios (i.e., inlet mole ratio=inlet $NH_3$/inlet $NO_x$) of 0.6, 0.8, 1.0, and 1.2; 360° C.; and fluid inflow rate of 6 m/s. The results are shown in Table 1 and FIG. 2.

Figure 2:
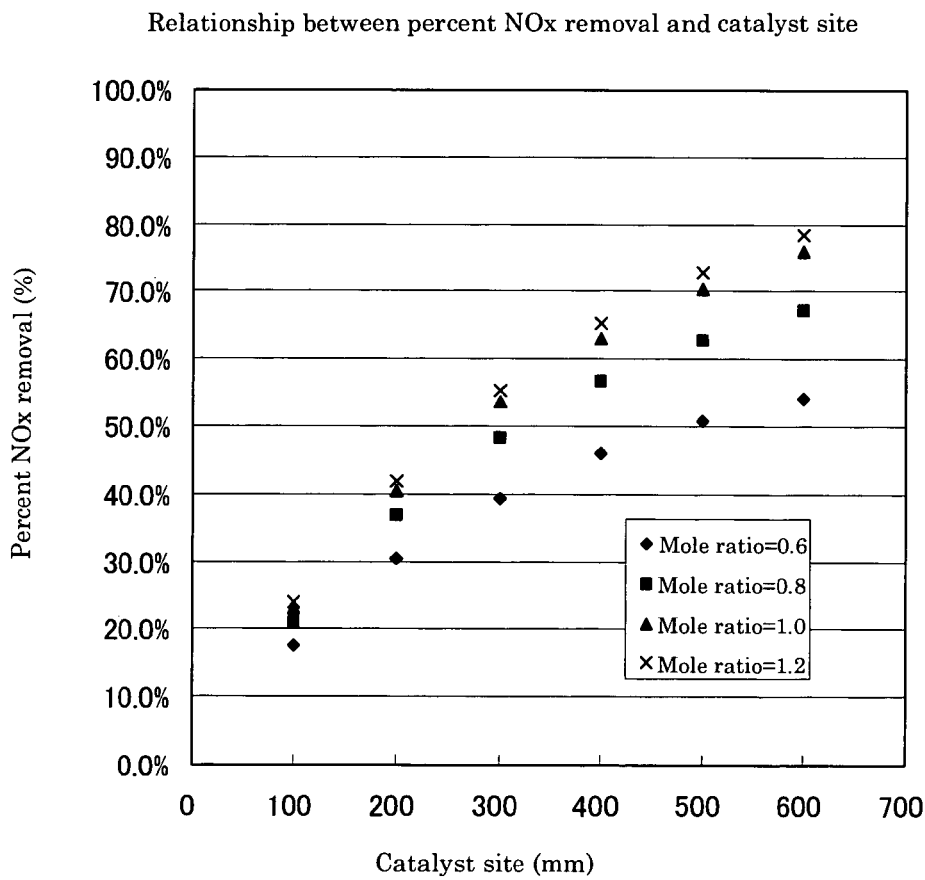
FIG. 2
A graph showing the results of Preliminary Test 2.

As is clear from Table 1 and FIG. 2, percent $NO_x$ removal tends to increase in proportion to the distance from the inlet (i.e., length of the catalyst) and that the increase in percent $NO_x$ removal tends to be suppressed when the catalyst length exceeds a certain value. The tendency is attributable to the flow of exhaust gas being gradually straightened.

TABLE 1

|  | 100 mm | 200 mm | 300 mm | 400 mm | 500 mm | 600 mm |
|---|---|---|---|---|---|---|
| Mole ratio 0.6 | 17.7 | 30.4 | 39.5 | 46.1 | 50.8 | 54.2 |
| Mole ratio 0.8 | 21.3 | 36.9 | 48.3 | 56.7 | 62.9 | 67.4 |
| Mole ratio 1.0 | 23.2 | 40.5 | 53.5 | 63.2 | 70.5 | 75.9 |
| Mole ratio 1.2 | 24.0 | 42.0 | 55.4 | 65.4 | 73.0 | 78.6 |

<Preliminary Test 3>

A honeycomb catalyst (600 mm×6 mm×6 mm, aperture size: 6 mm (pitch: 7 mm)) was subjected to simulation under the following conditions: 350° C. and fluid inflow rate (Uin): 4, 6, and 10 m/s.

Figure 3:
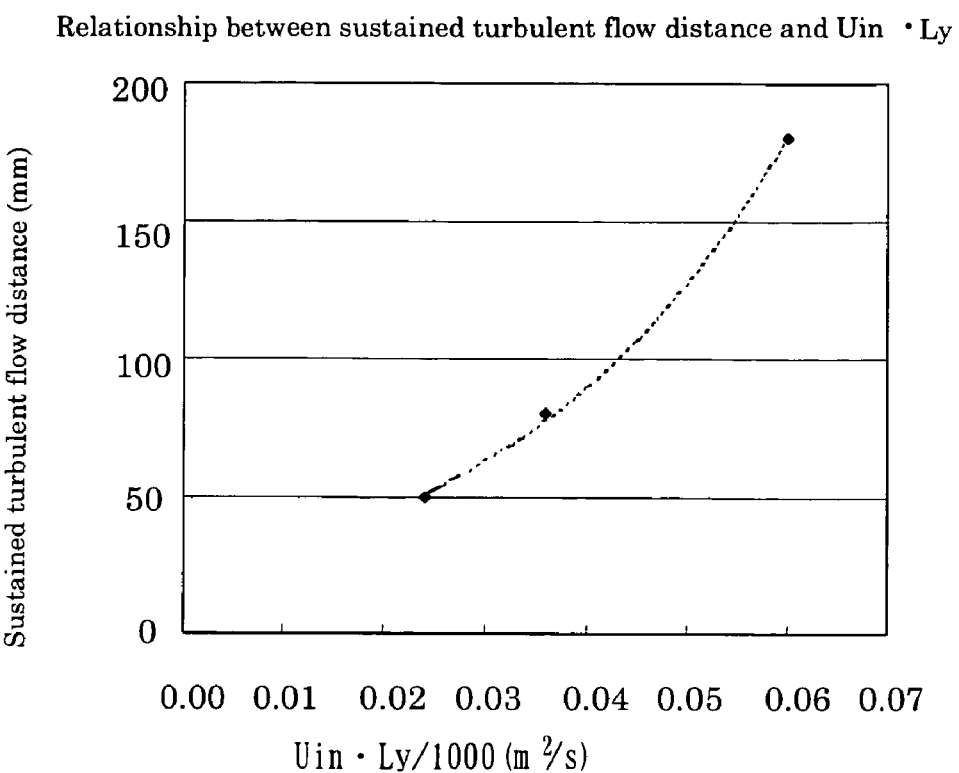
FIG. 3
A graph showing the results of Preliminary Test 3.

Through simulation, Uin and the distance from the inlet to a site where turbulent flow energy is lost in the course of transition from turbulent flow to laminar flow (hereinafter referred to as sustained turbulent flow distance (Lts)) were found to have the relationship shown in FIG. 3. Specifically, sustained turbulent flow distance (Lts) values at fluid inflow rates (Uin) of 4, 6, and 10 m/s were calculated as 50, 80, and 180 mm, respectively.

Theoretically, conditions of fluid are generally determined from inflow rate (Uin) and Reynolds number Re; i.e., a parameter employing aperture size Ly (Re=Uin·Ly/ν, ν=5.67×10$^{-5}$ m$^2$/S; constant).

In a honeycomb catalyst having an aperture size of 6 mm, sustained turbulent flow distance Lts (mm) is derived from a product of inflow rate Uins (m/s) and aperture size Lys (mm). Thus, the relationship between sustained turbulent flow distance Lts and a product of inflow rate Uins (Uin) and aperture size Lys (Ly), as shown in FIG. 3, was obtained. Through the least squares method, sustained turbulent flow distance Lts at an aperture size (Lys) of 6 mm is approximately represented by the following equation (1).

[F3]
$$Lts = 22e^{0.035(Lys \cdot Uins)} \qquad (1)$$

When the aperture size Lys is 6 mm (constant value), the aperture size Ly (mm) is an arbitrary parameter, and Uin (m/s) represents a gas inflow rate, sustained turbulent flow distance Lt can be represented by the following formula (2), which is a general equation.

[F4]
$$Lt = Ly/Lys \cdot 22e^{0.035(Ly \cdot Uin)} \qquad (2)$$

Figure 4:
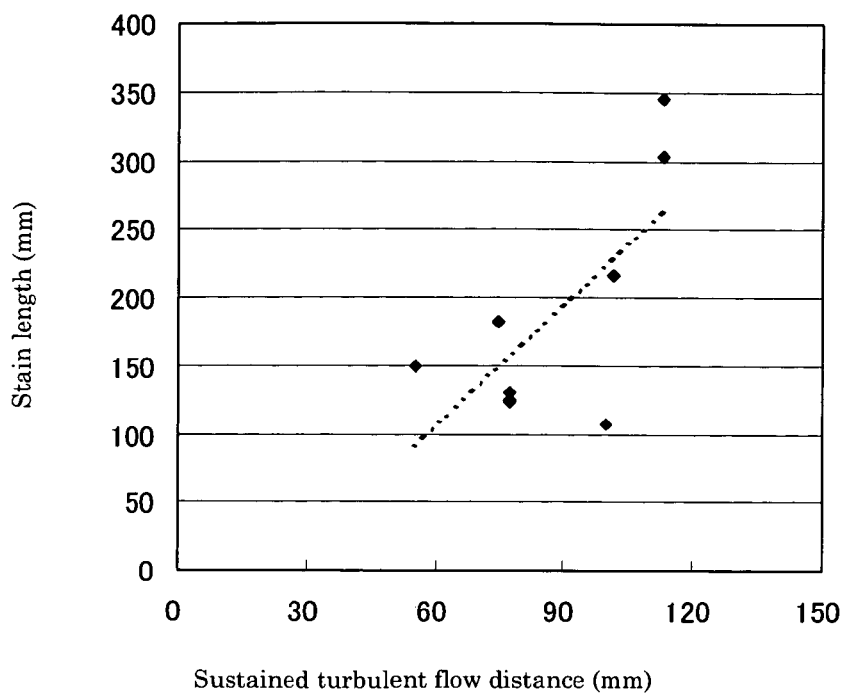
FIG. 4
A graph showing the results of Preliminary Test 3.

The simulation results were compared with the approximate length (optimum length) of the actual catalyst, the length being such that the flow of the exhaust gas fed into the gas conduits is straightened. Specifically, the relationship between sustained turbulent flow distance Lt and the optimum length of an actual catalyst (i.e., the length of a stained portion of the catalyst (stain length), which is an index for detecting straightening) was investigated. As shown in FIG. 4, in an actual stage of the employed apparatus, turbulent flow is maintained over a portion of the catalyst having a distance longer than the sustained turbulent flow distance Lt, which is derived through simulation. One possible reason of this phenomenon is that inflow rate is varied and flow of the fluid is disturbed.

Accordingly, in an actual catalyst unit, the distance from the inlet to a site where straightening starts (i.e., the length of the turbulent flow zone) must be determined from the above stain length and a certain safety length. Specifically, equation (2) must be multiplied by a constant "a," and the length of the turbulent flow zone of the actual catalyst Lb is considered to be represented by the following equation (3). Note that "a" is a constant falling within a range of 3 to 6, when the aperture size of a honeycomb catalyst is 6 mm (pitch: 7 mm) and the gas inflow rate is 6 m/s.

[F5]
$$Lb = a \cdot Lt \qquad (3)$$

In the aforementioned Test Example 1, a honeycomb catalyst having an aperture size of 6 mm (pitch: 7 mm) was used at a gas inflow rate of 6 m/s. Thus, Lt is 80 mm. When the constant "a" is adjusted to about 3.8, Lt is about 300 mm, which corresponds to the length of a severely deteriorated portion of the catalyst, whereas when the constant "a" is adjusted to about 5.6, Lt is about 450 mm, which corresponds to the length of a portion of the catalyst including a portion exhibiting catalytic performance equivalent to that of a new catalyst product.

In the same honeycomb catalyst, when "a" falls within a range of 3 to 6, the turbulent flow zone length Lb falls within a range of about 240 to 480 mm. The range of Lb virtually coincides with a range of about 300 to 450 mm, which is considered to be a length of an actual $NO_x$ removal catalyst portion where severe deterioration occurs and the discharge gas forms a turbulent flow in the gas conduits. Thus, the turbulent flow zone length Lb is selected from the range of 240 to 480 mm, corresponding to the "a" value of 3 to 6.

<Summary of the Preliminary Tests>

On the basis of the aforementioned test results, the length of the turbulent flow zone of a honeycomb $NO_x$ removal catalyst can be represented by the following equation:

[F6]

$$Lb = a(Ly/Lys \cdot 22 e^{0.035(Ly \cdot U/in)}) \quad (A)$$

(wherein "a" is a constant falling within a range of 3 to 6, when the aperture size (Ly) is 6 mm and the gas inflow rate is 6 m/s).

According to the method of the present invention, a first test piece, which is a catalyst portion having a length longer than the length of the turbulent flow zone; i.e., a length covering a turbulent flow zone and at least a portion of a laminar flow zone on the downstream side, is provided, the first test piece is subjected to a first $NO_x$ removal test (performance evaluation of the turbulent flow zone and the laminar flow zone); a second $NO_x$ removal test is performed on a second test piece, which is obtained through removal of a portion corresponding to the turbulent flow zone; and, on the basis of the test results, catalytic performance of an actual $NO_x$ removal catalyst is assessed. More specifically, performance of the turbulent flow zone can be assessed through the second $NO_x$ removal test, and performance of a portion of the laminar flow zone can be assessed through the first $NO_x$ removal test. Through extrapolation of catalyst length to the actual length, performance of the entire laminar flow zone can be assessed. The test piece for exclusively evaluating the turbulent flow zone is preferably cut from the test piece for the first $NO_x$ removal test. However, alternatively, the test piece may be cut from another, uncut catalyst sample. The first $NO_x$ removal test may be performed with a test piece including a portion of the laminar flow zone, or the test piece may contain the entirety of the laminar flow zone. In the latter case, extrapolation is not needed.

<$NO_x$ Removal Tests>

No particular limitation is imposed on the $NO_x$ removal tests carried out in the method of the present invention, and conventional test methods may be appropriately employed.

In the $NO_x$ removal tests, gas composition and gas inflow rate are preferably equivalent to those employed in an actual $NO_x$ removal apparatus. Even in the case where a gas inflow rate differing from that employed in the actual $NO_x$ removal apparatus is employed, as described hereinbelow, catalytic performance of the actual $NO_x$ removal apparatus can be assessed on the basis of the relationship between gas inflow rate and reacted $NO_x$.

In one exemplary catalytic performance assessment method, inlet and outlet $NO_x$ concentrations are determined, and percent $NO_x$ removal η and percent $NO_x$ removal contribution of the catalyst are calculated on the basis of the following equation. This technique is based on the method disclosed in Japanese Patent Publication (kokoku) No. 7-47108.

[F7]

$$\eta = \{(\text{inlet } NO_x - \text{outlet } NO_x)/(\text{inlet } NO_x)\} \times 100$$

In another catalytic performance assessment method, the inlet side and outlet side $NO_x$ concentrations and $NH_3$ concentrations are determined, and, if required, the inlet $O_2$ concentration is further determined. From the thus-obtained data, percent $NO_x$ removal η and percent $NO_x$ removal contribution of the catalyst are calculated. The percent $NO_x$ removal η is calculated on the basis of an inlet mole ratio (i.e., inlet $NH_3$/inlet $NO_x$) of the $NO_x$ removal catalyst. The reason for taking the inlet mole ratio into consideration is as follows. $NH_3$ is fed into an $NO_x$ removal apparatus in the vicinity of an $NO_x$ removal catalyst on the upstream side in an amount proportional to that of the gas to be treated. The rate determining step of $NO_x$ removal reaction is a step of adsorbing an $NH_3$ onto the catalyst. Therefore, determining $NH_3$ concentrations on the inlet and outlet sides of the $NO_x$ removal catalyst is most critical.

When calculated on the basis of an inlet mole ratio, the percent $NO_x$ removal η may be calculated from $NO_x$ concentration or $NH_3$ concentration. However, $NH_3$-basis calculation provides percent $NO_x$ removal values of higher precision suitable for management.

An exemplary procedure of deriving percent $NO_x$ removal η will next be described. The percent $NO_x$ removal η is determined on the basis of the following equation employing $NO_x$ concentrations.

[F8]

$$\eta = \{(\text{inlet } NO_x - \text{outlet } NO_x)/(\text{inlet } NO_x)\} \times 100 \times (\text{evaluation mole ratio/inlet mole ratio})$$

As used herein, the term "evaluation mole ratio" refers to a mole ratio which is predetermined for the purpose of evaluating an $NO_x$ removal catalyst. The evaluation mole ratio may be predetermined to an arbitrary value; for example, 0.8, which is almost equal to a mole ratio typically employed for operating a power station.

Although the percent $NO_x$ removal η is determined on the basis of the equation employing $NO_x$ concentrations, a target catalyst can be evaluated on the basis of a percent $NO_x$ removal value actually reflecting the conditions of the catalyst, since the equation employs an inlet mole ratio. In general, since the percent $NO_x$ removal η increases with $NH_3$/$NO_x$, the percent $NO_x$ removal η must be derived on the basis of the inlet mole ratio so as to evaluate a catalyst in an actual state.

The percent $NO_x$ removal η is also determined on the basis of the following equation employing $NH_3$ concentrations.

[F9]

$$\eta = \{(\text{inlet } NH_3 - \text{outlet } NH_3)/(\text{inlet } NH_3 - \text{outlet } NH_3 + \text{outlet } NO_x)\} \times 100 \times (\text{evaluation mole ratio/inlet mole ratio})$$

Since the percent $NO_x$ removal η is determined on the basis of the equation employing $NH_3$ concentrations, variation in the obtained percent $NO_x$ removal values is smaller as compared with the case in which the equation employing $NO_x$ concentrations is used, which is advantageous. Thus, catalysts can be evaluated on the basis of percent removal values with smaller variation.

Test Example

Figure 5:
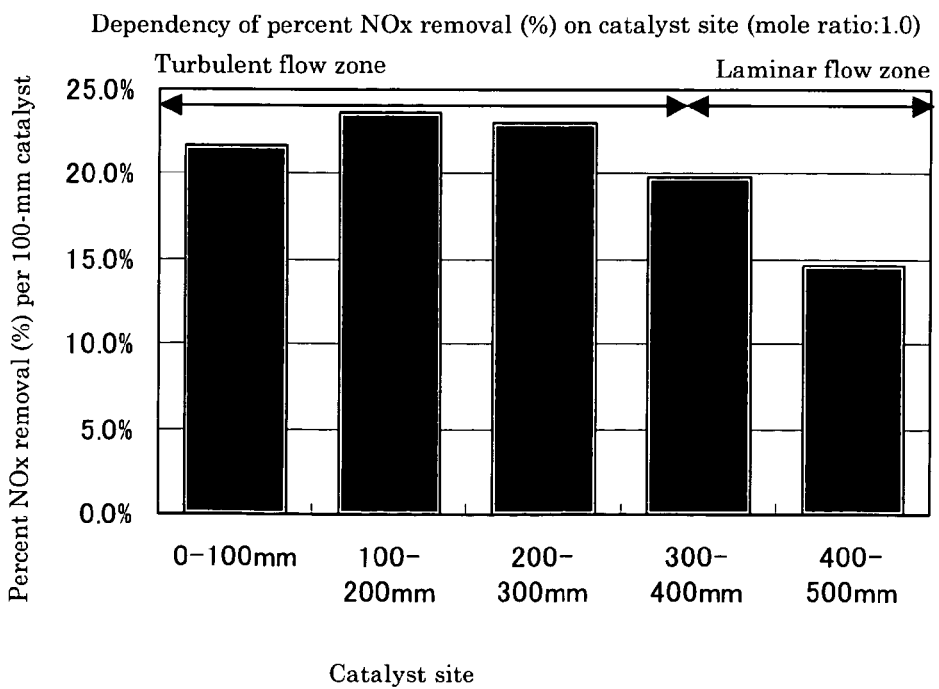
FIG. 5
A graph showing the results of Performance Test of the present invention.

Percent $NO_x$ removal of a honeycomb $NO_x$ removal catalyst new product was determined in five divided portions; i.e., portions each having a length of 100 mm, from the inlet (0 mm) to a site at 500 mm. The percent $NO_x$ removal was determined under the following conditions: flow rate in the honeycomb of 6 m/s, SV value (only in the case of 0-100 mm portion test piece) of 59,600 $m^3N/m^3$ h, AV value of 139.7 $m^3N/m^2$ h, reaction gas temperature of 360° C., and mole ratio of 1.0. Under these conditions, flows $NH_3$ and $NO_2$ were equalized. FIG. 5 shows the results.

As is clear from FIG. 5, $NO_x$ removal was found to be deteriorated from the site around the sustained turbulent flow distance (i.e., 300 to 400 mm).

Figure 6:
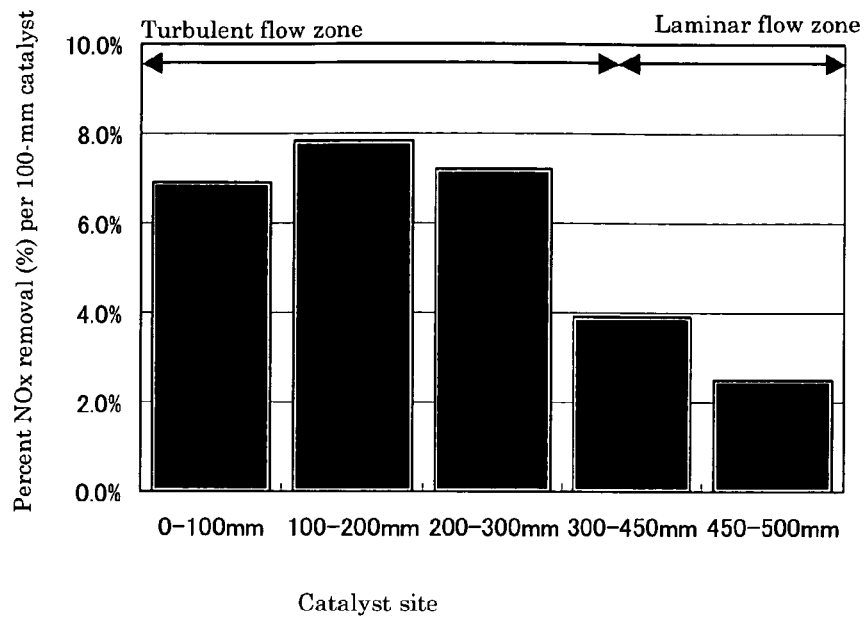
FIG. 6
A graph showing the results of Performance Test of the present invention.

In addition to the above new catalyst product, a used $NO_x$ removal catalyst was tested in a similar manner. FIG. 6 shows the results.

As is clear from FIG. 6, almost the same performance deterioration features as those of the new product were observed for the used $NO_x$ removal catalyst.

Example 1

A first test piece (600 mm) was cut from a used $NO_x$ removal catalyst (original length: 770 mm), and the test piece was subjected to a $NO_x$ removal test (a first $NO_x$ removal test). Subsequently, a second test piece (300 mm) was cut from the first test piece, and subjected to a similar $NO_x$ removal test.

Figure 7:
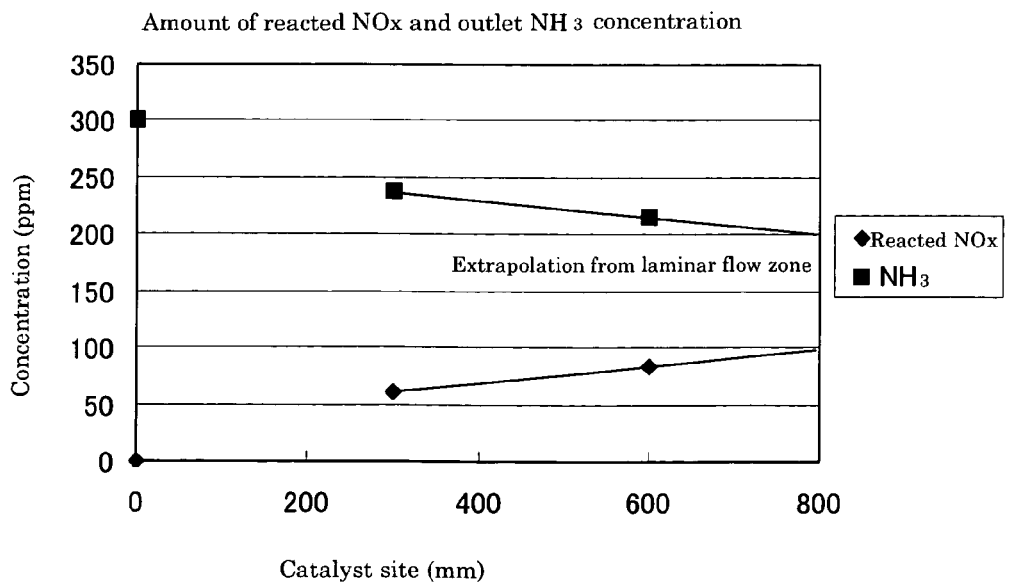
FIG. 7
A graph showing the results of Example 1 of the present invention.

Table 2 and FIG. 7 show the results. As is clear from FIG. 7, reacted $NO_x$ concentrations and $NH_3$ concentrations at catalyst sites of 300 mm and 600 mm were extrapolated to a catalyst site of 770 mm. Percent $NO_x$ removal at a catalyst site of 770 mm was determined from the extrapolated $NO_x$ concentration and $NH_3$ concentration.

TABLE 2

|  | 0 mm | 0-300 mm | 0-600 mm | Extrapolated |
|---|---|---|---|---|
| Catalyst site | 0 | 300 | 600 | 770 |
| Reacted $NO_x$ | 0 | 61 | 84 | 97 |
| $NH_3$ | 300 | 239 | 216 | 203 |
| % $NO_x$ removal | 0.0% | 20.3% | 28.0% | 32.3% |

Example 2

A first test piece (500 mm) was cut from an unused $NO_x$ removal catalyst, and the test piece was subjected to a $NO_x$ removal test (a first $NO_x$ removal test). Subsequently, a second test piece (300 mm) was cut from the first test piece, and subjected to a similar $NO_x$ removal test.

Figure 8:
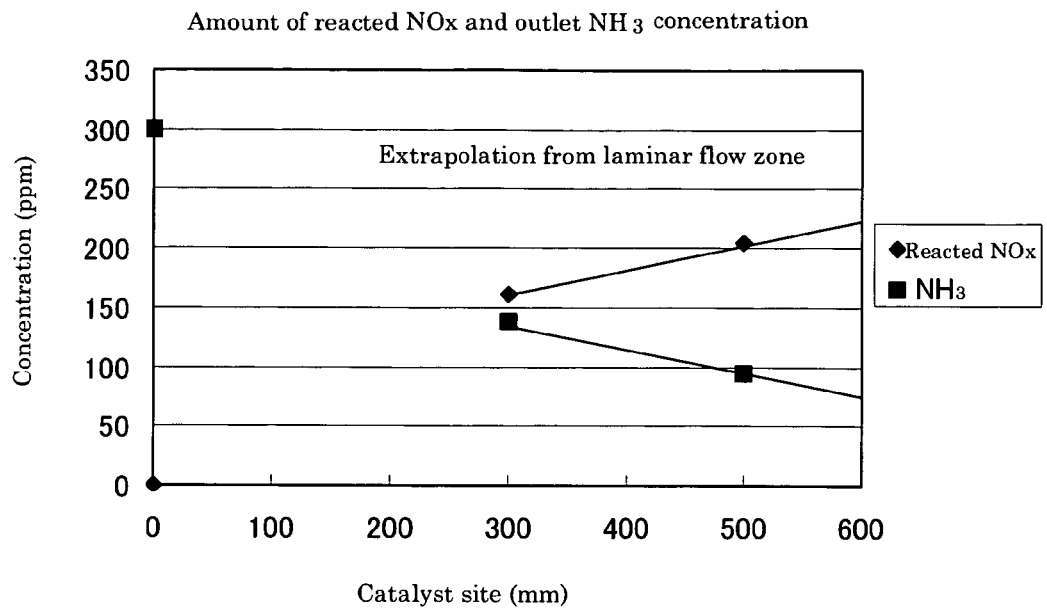
FIG. 8
A graph showing the results of Example 2 of the present invention.

Table 3 and FIG. 8 show the results. As is clear from FIG. 8, reacted $NO_x$ concentrations and $NH_3$ concentrations at catalyst sites of 300 mm and 500 mm were extrapolated to catalyst sites of 770 mm and 800 mm. Percent $NO_x$ removal values at catalyst sites of 770 mm and 800 mm were determined from the extrapolated $NO_x$ concentrations and $NH_3$ concentrations.

Actual percent $NO_x$ removal was determined at catalyst sites of 770 mm and 800 mm so as to evaluate the extrapolated values. Table 3 shows the thus-determined percent $NO_x$ removal values.

As is clear from Table 3, the extrapolated values obtained according to the present invention and the actually determined values were found to be virtually equivalent.

TABLE 3

|  | 0 mm | 0-300 mm | 0-500 mm | Extrapolated | Measured | Extrapolated | Measured |
|---|---|---|---|---|---|---|---|
| Catalyst site | 0 | 300 | 500 | 770 |  | 800 |  |
| Reacted $NO_x$ | 0 | 162 | 205 | 264 | — | 271 | — |
| $NH_3$ | 300 | 138 | 95 | 36 | — | 29 | — |
| % $NO_x$ removal | 0 | 54.0% | 68.5% | 88.0% | 85.6% | 90.2% | 89.1% |

Example 3

Catalyst test pieces (300 mm and 500 mm) were evaluated in terms of amount of reacted $NO_x$. The measurement was performed at 360° C. and at mole ratios (inlet mole ratios (i.e., inlet $NH_3$/inlet $NO_x$)) of 0.6, 0.8, 1.0, and 1.2 and gas inflow rates of 6 m/s and 9 m/s.

Figure 9:
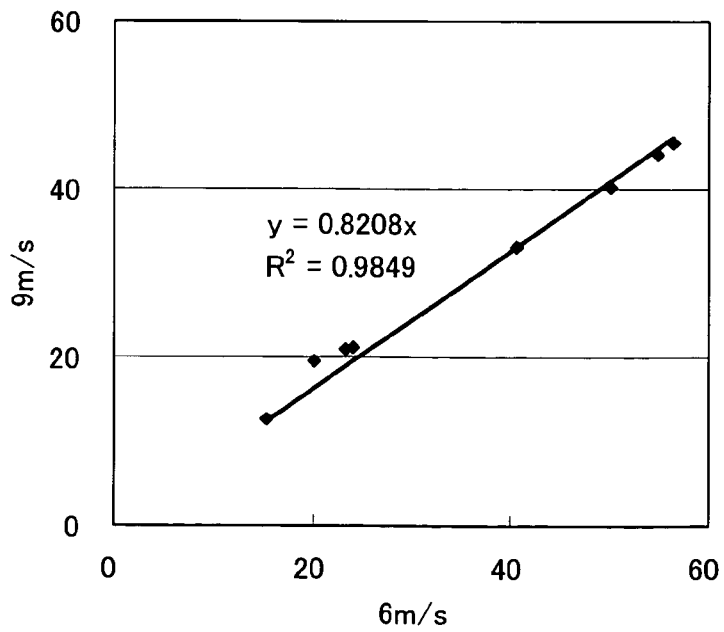
FIG. 9
A graph showing the results of Example 3 of the present invention.

Table 4 and FIG. 9 show the results. As is clear from Table 4 and FIG. 9, a reacted $NO_x$ amount at a gas inflow rate of v1 (reacted $NO_{x(v1)}$) and a reacted $NO_x$ amount at a gas inflow rate of v2 (reacted $NO_{x(v2)}$) have the following relationship. Thus, when a gas inflow rate differing from that employed in an actual $NO_x$ removal apparatus is employed, catalytic performance can be determined by converting, on the basis of the following equation, the reacted $NO_x$ amount determined under the above conditions to the corresponding value at a gas inflow rate employed in the actual $NO_x$ removal apparatus.

[F10]

$$(\text{Reacted } NO_{x(v1)}/100\text{-mm catalyst piece}) \times v1^{0.5} = (\text{reacted } NO_{x(v2)}/100\text{-mm catalyst piece}) \times v2^{0.5}$$

TABLE 4

| Catalyst piece length | Mole ratio | Gas inflow rate 6 m/s | Gas inflow rate 9 m/s |
|---|---|---|---|
| 300 mm | 0.6 | 41 | 33 |
|  | 0.8 | 50 | 40 |
|  | 1.0 | 55 | 44 |
|  | 1.2 | 56 | 46 |
| 500 mm | 0.6 | 15 | 13 |
|  | 0.8 | 20 | 19 |
|  | 1.0 | 23 | 21 |
|  | 1.2 | 24 | 21 |

INDUSTRIAL APPLICABILITY

The present invention can be suitably applied to assessment of performance of $NO_x$ removal catalysts employed in a flue gas $NO_x$ removal apparatus installed in a facility such as a thermal power station and $NO_x$ removal catalysts employed in boilers.

The invention claimed is:

1. A method of testing a honeycomb-form $NO_x$ removal catalyst for use in a flue gas $NO_x$ removal apparatus, the catalyst having gas conduits for feeding a discharge gas from an inlet to an outlet of each conduit and performing $NO_x$ removal on the sidewalls of the conduit, characterized in that the method comprises providing a first test piece, which is a portion of the catalyst having a length covering the entirety of a turbulent flow zone in which a gas to be treated that has been fed into the gas conduits through the inlet of the $NO_x$ removal catalyst forms a turbulent flow and further covering at least a portion of a laminar flow zone in which the turbulent flow is rectified to form a laminar flow;

performing a first $NO_x$ removal test of the provided first test piece;

subsequently, performing a second $NO_x$ removal test of a second test piece, which is obtained through cutting out a catalyst portion of a length covering the turbulent flow zone; and assessing, on the basis of the test results, catalytic performance of the turbulent flow zone and that of the laminar flow zone, whereby catalytic performance of the $NO_x$ removal catalyst is assessed.

2. A method of testing a honeycomb-form $NO_x$ removal catalyst according to claim 1, wherein the turbulent flow zone has a length Lb (mm) represented by equation (A):

[F1]

$$Lb = a(Ly/Lys \cdot 22 e^{0.035(Ly \cdot Uin)}) \quad (A)$$

(wherein Uin (m/s) represents a gas inflow rate, Ly (mm) represents an aperture size, Lys is an aperture size of 6 mm (constant value), and "a" is a constant falling within a range of 3 to 6, when the aperture size (Ly) is 6 mm and the gas inflow rate is 6 m/s).

3. A method of testing a honeycomb-form $NO_x$ removal catalyst according to claim 1, wherein the first and second $NO_x$ removal tests are performed while a model gas having a composition simulating the gas treated in an actual $NO_x$ removal apparatus is fed at a gas inflow rate equivalent to that employed in an actual $NO_x$ removal apparatus, thereby determining catalyst performance.

4. A method of testing a honeycomb-form $NO_x$ removal catalyst according to claim 1, wherein the first and second $NO_x$ removal tests are performed while a model gas having a composition simulating the gas treated in an actual $NO_x$ removal apparatus is fed at a flow rate differing from that employed in an actual $NO_x$ removal apparatus, thereby determining catalyst performance in consideration of the relationship between gas inflow rate and reacted $NO_x$.

5. A method of testing a honeycomb-form $NO_x$ removal catalyst according to claim 1, wherein the first and second $NO_x$ removal tests comprise determining $NO_x$ concentrations on the inlet and outlet sides of respective test pieces; determining $NH_3$ concentrations on the inlet and outlet sides of respective test pieces; and determining percent $NO_x$ removal η on the basis of an inlet mole ratio (i.e., inlet $NH_3$/inlet $NO_x$).

6. A method of testing a honeycomb-form $NO_x$ removal catalyst according to claim 5, wherein the percent $NO_x$ removal η is determined on the basis of $NH_3$ concentrations.

7. A method of testing a honeycomb-form $NO_x$ removal catalyst according to claim 6, wherein the percent $NO_x$ removal η is determined on the basis of the following equation:

[F2]

$$\eta = \{(\text{inlet } NH_3 - \text{outlet } NH_3)/(\text{inlet } NH_3 - \text{outlet } NH_3 + \text{outlet } NO_x)\} \times 100 \times (\text{evaluation mole ratio/inlet mole ratio}).$$

* * * * *